US00PP15046P2

(12) United States Plant Patent
Bessho

(10) Patent No.: US PP15,046 P2
(45) Date of Patent: Jul. 27, 2004

(54) CALIBRACHOA PLANT NAMED 'KAKEGAWA S52'

(50) Latin Name: *Calibrachoa parviflora*
Varietal Denomination: Kakegawa S52

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 23 days.

(21) Appl. No.: 10/402,380

(22) Filed: Mar. 28, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Jondle & Associates P C

(57) ABSTRACT

'Kakegawa S52' is a new variety of Calibrachoa plant. This new variety has pale red colored flowers and dark green foliage.

1 Drawing Sheet

BACKGROUND OF THE INVENTION

'Kakegawa S52' originated from a hybridization made in November 1998 in Kakegawa, Japan. The female parent was a Calibrachoa breeding line with orange-red colored flowers and erect habit known as K7-1160 (not patented). The male parent was Calibrachoa breeding line with white flowers and a ring at the corolla throat and creeping plant habit known as 97-1101-1 (not patented).

In February 1999, $F_1$ seed was sown from this cross and 30 plants were transplanted to outdoors. Four plants were selected for creeping and branching habit and intercrossed to produce $F_2$ seed. In August 1999 the second generation seed was planted in the field at Kakegawa and plants with different shades of red, orange and pink flowers were observed. Two plants with coral colored flowers were selected. In February 2000 these plant lines were then vegetatively propagated and grown to flowering stage in pots. Trait stability was evaluated during the summer of 2000 in greenhouses in Japan.

The breeder selected one line, for flower color and abundance, to be vegetatively propagated and further evaluated during 2001 at Kakegawa. 'Kakegawa S52' and was determined to have its trait characteristics firmly fixed.

DESCRIPTION OF PHOTOGRAPH

This new Calibrachoa plant is illustrated by the accompanying photographs which show blooms, and foliage of the plant in full color, the colors shown being as true as can be reasonably obtained by conventional photographic procedures.

Figure 1:
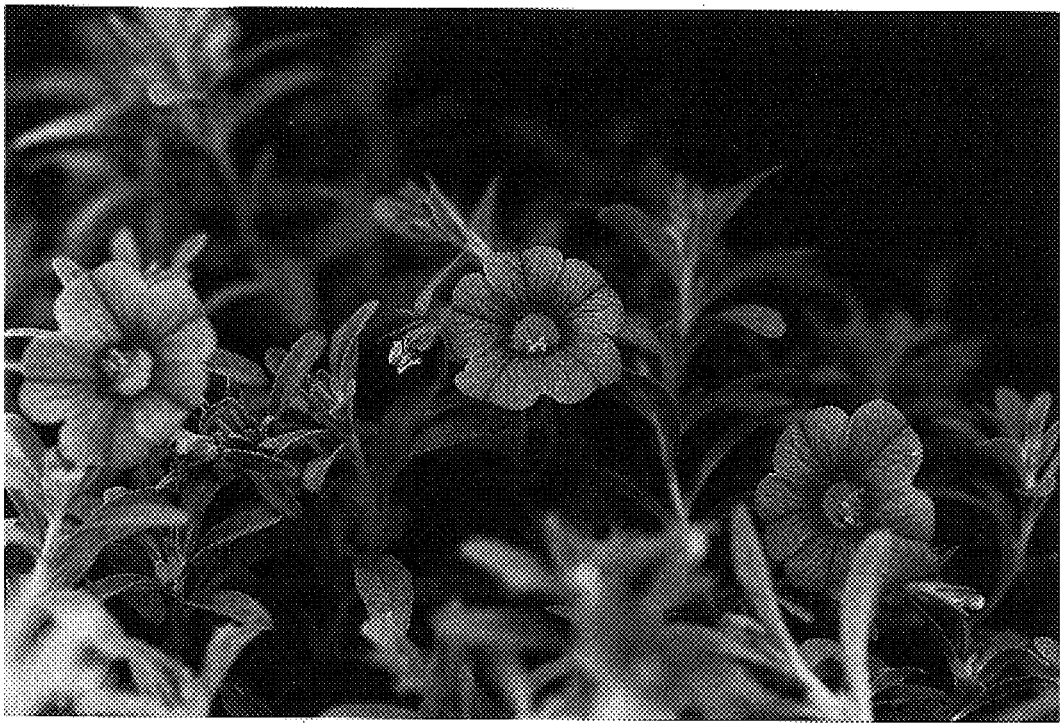
FIG. 1 shows the mature inflorescence.
Figure 2:
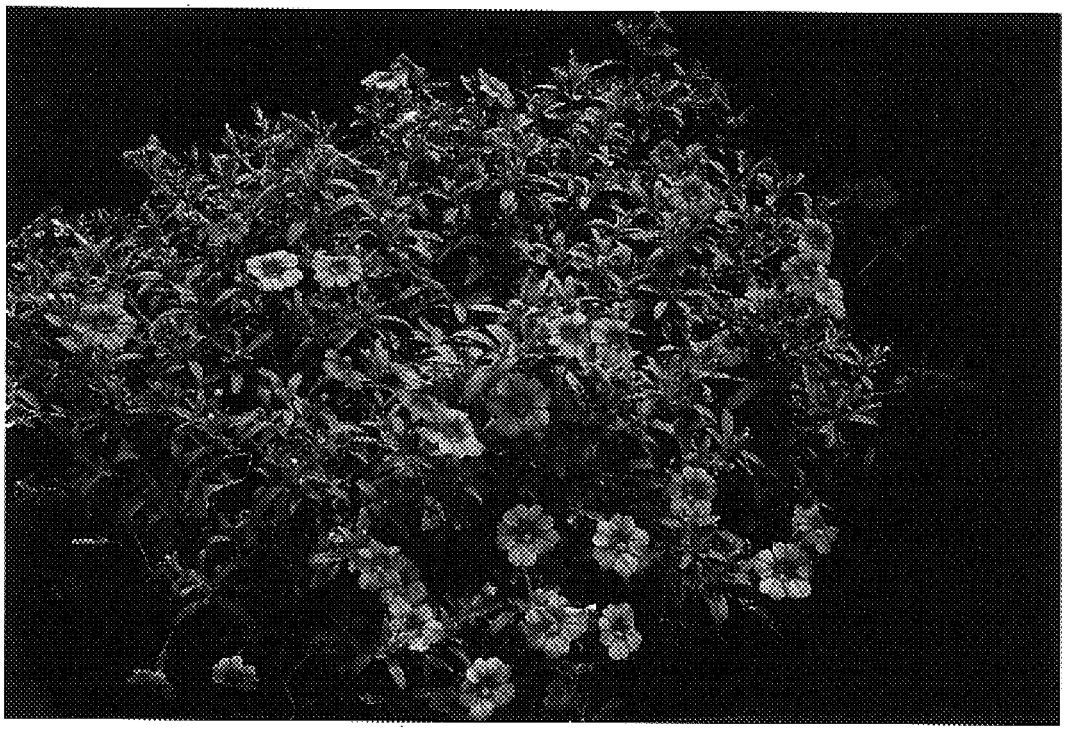
FIG. 2 shows the entire plant.

Description of the genus Calibrachoa Llave & Lex

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida*, the Garden Petunia, and the inter-relationship of several species classified as Petunia. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I.N.G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of Dip 'N Grow (1 Dip 'N Grow: 9 water) root inducing solution immediately prior to sticking into the cells trays. Cuttings were stuck into plastic cell trays having 98 cells, and containing a moistened peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse. Pots contained a peat moss-based growing medium. Soluble fertilizer containing 20% nitrogen, 10% phosphorus and 20% potassium was applied once a day or every other day. Fertilizer was applied in irrigation water. Pots were top-dressed with a slow release fertilizer containing 20% nitrogen, 10% phosphorus and 18% potassium. The typical average air temperature was 24C.

DETAILED DESCRIPTION OF THE NEW PLANT

The following traits and characteristics describe the new variety.

Classification:
- *Family.*—Solanaceae.
- *Species.*—Calibrachoa spp.
- *Common names.*—Petunia.

Parentage:
- *Female parent.*—Breeding line K7-1160 (not patented).
- *Male parent.*—Breeding line 97-1101-1 (not patented).

Growth:
- *Habit.*—decumbent.
- *Height.*—23.0 cm.
- *Spread.*—115.0 cm when grown in a 41 cm hanging basket or pot, and using five 20 cm potted plants in one hanging basket.
- *Life cycle.*—Tender perennial.
- *Time to produce a rooted cutting.*—6 weeks.
- *Time to bloom from propagation.*—10 weeks.
- *Flowering season.*—Spring and summer.
- *Flowering requirements.*—No particular requirements, day neutral.
- *Resistance/susceptibility.*—Excellent resistance to rain, heat and drought. Will not tolerate temperatures below 10C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.
- *Form.*—Branching, dense.

Stems:
- *Stem color.*—R.H.S. 138B (yellow—green).
- *Pubescence.*—Slight.
- *Pubescence color.*—Clear.
- *Pubescence shape.*—Pointed.
- *Stem description.*—Round, slightly, ancipital.
- *Stem diameter.*—1.5 mm.
- *Internode length.*—2.0 to 3.0 cm.

Leaves:
- *Leaf tip.*—Mucronate.
- *Leaf arrangement.*—Alternate.
- *Leaf base.*—Decurrent.
- *Leaf color.*—Upper surface: R.H.S. 137B (green); lower surface: R.H.S. 138C (green).
- *Leaf fragrance.*—Absent.
- *Leaf Margin.*—Entire.
- *Leaf surface.*—Rough.
- *Leaf surface pubescence.*—Slight.
- *Petiole color.*—R.H.S. 138B (green).
- *Petiole length.*—3.0 mm.
- *Leaf length.*—2.5–3.0 cm.
- *Leaf shape.*—Elliptical.
- *Leaf width.*—6.0 mm–8.0 cm.

Flowers:
- *Calyx.*—5 sepals; 7.0×3.0 mm (l×w); free.
- *Corolla.*—5 petals, fused.
- *Flower diameter.*—2.8 cm.
- *Bud color.*—R.H.S. 150B (yellow—green).
- *Bud shape.*—Ovate.
- *Bud surface.*—Pubescent.
- *Ovary.*—Superior.
- *Duration of flower life.*—5 days.
- *Flowering habit.*—Indeterminate.
- *Placenta arrangement.*—Central.
- *Peduncle size.*—1.0 mm diameter; 3.0 mm length, slightly, short pubescence.
- *Inflorescence type.*—Solitary.
- *Stamens.*—Free.
- *Stamen color.*—R.H.S. 149D (yellow-green).
- *Stigma color.*—R.H.S. 149C (yellow-green).
- *Style color.*—R.H.S. 149C (yellow-green).
- *Petal size.*—2.0 cm×2.0 cm (1×w).
- *Petal color.*—Upper surface: R.H.S. 48C (red) with R.H.S. 47A(red) corolla throat and mid-veins; lower surface: R.H.S. 50A (red); corolla tube: inner surface: R.H.S. 5A (yellow); outer surface: R.H.S. 6A (yellow).
- *Pollen color.*—R.H.S. 9B (yellow).
- *Produces seed.*—None.

COMPARISON WITH MOST SIMILAR VARIETY

'Kakegawa S52' is a distinct variety of Calibrachoa owing to its pale red flower with bright yellow tube and red corolla throat. 'Kakegawa S52' also possesses the unusual characteristic of the petal mid-veins being a different color from the petal itself. 'Kakegawa S52' is most similar to the variety 'Million Bells Terra Cotta' however there are numerous differences as shown in the table 1 below.

TABLE 1

| Characteristic | 'Kakegawa S52' | 'Million Bells Terra Cotta' |
|---|---|---|
| Leaf Length | 2.5 cm | 5.2 cm |
| Petal Color (upper) | RHS 48C (red) | RHS 9C (yellow) |
| Petal Color (lower) | RHS 50A (red) | RHS 66B (red-purple) |
| Petal Vein Color | RHS 47A (red) | RHS 45B (red) |

What is claimed is:

1. A new and distinct Calibrachoa plant as shown and described herein.

* * * * *